US012622577B2

(12) United States Patent　　　(10) Patent No.:　US 12,622,577 B2
Calabrese et al.　　　　　　　　(45) Date of Patent:　*May 12, 2026

(54) ENDOSCOPE HAVING MULTIPLE VIEWING DIRECTIONS

(71) Applicant: Boston Scientific Scimed, Inc., Maple Grove, MN (US)

(72) Inventors: Andrew Calabrese, Lancaster, MA (US); Louis J. Barbato, Franklin, MA (US); Brian Gaffney, Rutland, MA (US); Mark D. Wood, Sterling, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 18/624,222

(22) Filed: Apr. 2, 2024

(65) Prior Publication Data

US 2024/0268648 A1　　Aug. 15, 2024

Related U.S. Application Data

(63) Continuation of application No. 17/398,871, filed on Aug. 10, 2021, now Pat. No. 11,974,724, which is a
(Continued)

(51) Int. Cl.
*A61B 1/00*　　　　(2006.01)
*A61B 1/018*　　　(2006.01)
(Continued)

(52) U.S. Cl.
CPC .......... *A61B 1/051* (2013.01); *A61B 1/00087* (2013.01); *A61B 1/00096* (2013.01);
(Continued)

(58) Field of Classification Search
CPC ............ A61B 1/00087; A61B 1/00098; A61B 1/00181; A61B 1/018; A61B 1/05
See application file for complete search history.

(56) References Cited

U.S. PATENT DOCUMENTS 3,880,148 A　　4/1975　Kanehira et al.
4,195,904 A　　4/1980　Yamashita et al.
(Continued)

FOREIGN PATENT DOCUMENTS

CN　　101548874 B　　2/2011
CN　　104619265 A　　5/2015
(Continued)

OTHER PUBLICATIONS

Samir Sahli et al., "A 360 Degree Side View Endoscope for Lower GI Tract Mapping", Physics in Canada, vol. 71, No. 1, 2015, pp. 18-20.
(Continued)

*Primary Examiner* — Anh Tuan T Nguyen
*Assistant Examiner* — Shankar Raj Ghimire
(74) *Attorney, Agent, or Firm* — Bookoff McAndrews PLLC

(57) ABSTRACT

An endoscope may include a shaft having a longitudinal axis, a first image sensor facing a distal direction, and a second image sensor facing a lateral direction. The endoscope may further include a tubular member having a lumen, the lumen having a distal-end opening and defining a longitudinal axis through a center of the lumen. The tubular member may be movable between a first configuration and a second configuration. In the first configuration of the tubular member, the longitudinal axis of the lumen may be parallel to the longitudinal axis of the shaft. In the second
(Continued)

configuration of the tubular member, the longitudinal axis of the lumen may extend through a lateral opening in a wall of the shaft.

20 Claims, 3 Drawing Sheets

Related U.S. Application Data continuation of application No. 15/881,907, filed on Jan. 29, 2018, now Pat. No. 11,116,391.

(60) Provisional application No. 62/453,186, filed on Feb. 1, 2017.

(51) Int. Cl.
*A61B 1/05* (2006.01)
*A61B 1/06* (2006.01)

(52) U.S. Cl.
CPC ...... *A61B 1/00098* (2013.01); *A61B 1/00181* (2013.01); *A61B 1/018* (2013.01); *A61B 1/0615* (2013.01); *A61B 1/0669* (2013.01); *A61B 1/00172* (2013.01); *A61B 1/05* (2013.01)

(56) References Cited

U.S. PATENT DOCUMENTS

| | | | |
|---|---|---|---|
| 4,407,273 | A | 10/1983 | Ouchi |
| 5,730,701 | A | 3/1998 | Furukawa et al. |
| 6,450,950 | B2 | 9/2002 | Irion |
| 7,063,659 | B2 | 6/2006 | Goto et al. |
| 7,087,010 | B2 | 8/2006 | Ootawara et al. |
| 7,753,843 | B2 * | 7/2010 | Wood ................ A61B 1/00098 600/137 |
| 9,427,139 | B2 | 8/2016 | Tinkham et al. |
| 10,342,459 | B2 | 7/2019 | Yokota |
| 2002/0091303 | A1 | 7/2002 | Ootawara et al. |
| 2003/0073955 | A1 | 4/2003 | Otawara |
| 2004/0049095 | A1 | 3/2004 | Goto et al. |
| 2007/0118019 | A1 | 5/2007 | Mitani |
| 2007/0197871 | A1 | 8/2007 | Geitz et al. |
| 2007/0208220 | A1 | 9/2007 | Carter |
| 2007/0232857 | A1 | 10/2007 | Otawara |
| 2007/0249898 | A1 | 10/2007 | Otawara |
| 2007/0265499 | A1 | 11/2007 | Wood et al. |
| 2007/0293719 | A1 * | 12/2007 | Scopton ............. A61B 1/00098 600/106 |
| 2008/0021416 | A1 | 1/2008 | Arai et al. |
| 2008/0287961 | A1 * | 11/2008 | Miyamoto ............. A61B 1/018 606/127 |
| 2009/0182194 | A1 | 7/2009 | Wood et al. |
| 2012/0157773 | A1 | 6/2012 | Honda et al. |
| 2012/0253121 | A1 | 10/2012 | Kitano |
| 2013/0172670 | A1 | 7/2013 | Levy et al. |
| 2013/0172677 | A1 | 7/2013 | Kennedy, II et al. |
| 2013/0190562 | A1 | 7/2013 | Smith et al. |
| 2014/0364694 | A1 | 12/2014 | Avron et al. |
| 2015/0031946 | A1 | 1/2015 | Saadat et al. |
| 2015/0031947 | A1 | 1/2015 | Kudo et al. |
| 2015/0157384 | A1 | 6/2015 | Hoey et al. |
| 2015/0173711 | A1 * | 6/2015 | Hiraoka ............... A61B 1/0005 600/466 |
| 2015/0250377 | A1 | 9/2015 | Iizuka |
| 2016/0089003 | A1 * | 3/2016 | Morimoto .......... A61B 1/00177 600/107 |
| 2016/0089125 | A1 * | 3/2016 | Morimoto .......... A61B 1/00098 600/107 |
| 2016/0270634 | A1 | 9/2016 | Tanaka et al. |
| 2017/0014017 | A1 | 1/2017 | Obara et al. |
| 2017/0014116 | A1 | 1/2017 | Nakazato |
| 2017/0041537 | A1 | 2/2017 | Iwasaki et al. |
| 2017/0049300 | A1 | 2/2017 | Toyooka |
| 2017/0290566 | A1 | 10/2017 | Hosogoe |
| 2018/0160889 | A1 | 6/2018 | Hirano et al. |
| 2018/0310815 | A1 | 11/2018 | Tezuka et al. |
| 2019/0142242 | A1 | 5/2019 | Yamaya |
| 2019/0216299 | A1 | 7/2019 | Hayakawa |
| 2019/0223698 | A1 | 7/2019 | Hosogoe et al. |
| 2019/0231173 | A1 | 8/2019 | Hosogoe |
| 2020/0069153 | A1 | 3/2020 | Sueyasu |
| 2020/0146534 | A1 | 5/2020 | Harada |
| 2020/0352419 | A1 | 11/2020 | Hayakawa |
| 2020/0390322 | A1 * | 12/2020 | Saito .................. A61B 1/00098 |
| 2021/0290042 | A1 | 9/2021 | Hosogoe |

FOREIGN PATENT DOCUMENTS

| | | | |
|---|---|---|---|
| EP | 1955643 | A1 | 8/2008 |
| JP | 52-067184 | A | 6/1977 |
| JP | S52-141892 | U | 10/1977 |
| JP | H06-319682 | A | 11/1994 |
| JP | H07194524 | A | 8/1995 |
| JP | 8-140922 | A | 6/1996 |
| JP | H08243076 | A | 9/1996 |
| JP | 2000-116598 | A | 4/2000 |
| JP | 2003116777 | A | 4/2003 |
| JP | 2005-334275 | A | 12/2005 |
| JP | 2006015018 | A | 1/2006 |
| JP | 2006034457 | A | 2/2006 |
| JP | 2006-102325 | A | 4/2006 |
| JP | 2007330756 | A | 12/2007 |
| JP | 2010-12079 | A | 1/2010 |
| JP | 2010012079 | A * | 1/2010 ......... A61B 1/00098 |
| JP | 2010-178766 | A | 8/2010 |
| JP | 2011136193 | A | 7/2011 |
| JP | 51-050725 | B2 | 2/2013 |
| WO | 2011148894 | A1 | 12/2011 |
| WO | 2014136326 | A1 | 9/2014 |
| WO | 2015/151973 | A1 | 10/2015 |

OTHER PUBLICATIONS

Extended European search report in corresponding European Application No. 23173018.5, dated Jul. 12, 2023 (7 pages).

English Translation of Japanese Office Action dated Dec. 9, 2021, in counterpart Japanese Patent Application No. 2019-541253 (3 pages, in English).

Extended European Search Report issued on Jun. 8, 2021 in counterpart European Patent Application No. 21153724.6 (8 pages, in English).

\* cited by examiner

ENDOSCOPE HAVING MULTIPLE VIEWING DIRECTIONS

CROSS-REFERENCE TO RELATED APPLICATIONS

This patent application is a continuation of U.S. patent application Ser. No. 17/398,871, filed on Aug. 10, 2021, which is a continuation of U.S. patent application Ser. No. 15/881,907, filed on Jan. 29, 2018, now U.S. Pat. No. 11,116,391, which claims the benefit under 35 U.S.C. § 119 to U.S. Provisional Patent Application No. 62/453,186, filed on Feb. 1, 2017, the entireties of which are incorporated herein by reference.

TECHNICAL FIELD

The present disclosure relates generally to an endoscope having multiple viewing directions and an adjustable elevator to provide multiple working directions.

BACKGROUND

Endoscopic retrograde cholangiopancreatography (ERCP) is a procedure used to diagnose and treat patients with pancreatic-biliary disorders. ERCPs are commonly completed using a side viewing endoscope with an elevator mechanism. The layout of a side viewing scope and elevator feature allow the physician to cannulate the duodenal papilla and access a target site with tools for diagnostic and therapeutic ERCP procedures.

Forward viewing endoscopes are occasionally used in patients with altered anatomy, but since such endoscopes do not feature an elevator or a side viewing image sensor, the physician's diagnostic and therapeutic capabilities may be limited compared with using a side viewing endoscope having an elevator and a side viewing image sensor. In addition, the current commercially available forward viewing scopes may be longer than a side viewing scope and may require different cannulation methods and different tools to be used. The commercially available forward viewing endoscopes may succeed in certain patients with altered anatomy; however, their use may require changes to the physician's procedure and additional effort when compared to performing an ERCP with a side viewing scope.

SUMMARY

Examples of the present disclosure relate to, among other things, an endoscope having multiple viewing directions and an adjustable elevator (e.g., a tubular member) to provide multiple working directions. Each of the examples disclosed herein may include one or more of the features described in connection with any of the other disclosed examples.

In one example, an endoscope may include a shaft having a longitudinal axis, a first image sensor facing a distal direction, and a second image sensor facing a lateral direction. The endoscope may further include a tubular member having a lumen, the lumen having a distal-end opening and defining a longitudinal axis through a center of the lumen. The tubular member may be movable between a first configuration and a second configuration. In the first configuration of the tubular member, the longitudinal axis of the lumen may be parallel to the longitudinal axis of the shaft. In the second configuration of the tubular member, the longitudinal axis of the lumen may extend through a lateral opening in a wall of the shaft.

Any example of an endoscope described herein may further include one or more of the following features: the first image sensor may be positioned on a distal-facing wall of the shaft, and the second image sensor may be positioned on a lateral-facing wall of the shaft; in the first configuration, the distal-end opening may parallel to the distal-facing wall of the shaft; the distal-facing wall may positioned at a distal-most end of the shaft; the first image sensor may be adjustable relative to the distal-facing wall, and the second image sensor may be adjustable relative to the lateral-facing wall; the lateral-facing wall of the shaft may be flat, and the distal-facing wall and the lateral-facing wall may be perpendicular to each other; the distal direction and the lateral direction may be about 90° from each other; the endoscope may further include a medical device positioned within the tubular member, wherein in the first configuration, the medical device may extend from the distal-end opening of the tubular member, and the first image sensor may be configured to image the medical device; in the second configuration, the medical device may extend from the distal-end opening of the tubular member, and the second image sensor may be configured to image the medical device; the tubular member may be further movable to a third configuration, and in the third configuration, the medical device may be locked relative to the wall of the shaft; the endoscope may further include a first light source associated with the first image sensor, and a second light source associated with the second image sensor; the endoscope may further include a plurality of light sources; the wall of the shaft may include a distal-facing indentation configured to receive and secure a medical device relative to the wall of the shaft; in the first configuration of the tubular member, the longitudinal axis of the lumen may extend through a distal opening in the wall of the shaft; a range of motion of the tubular member may be at least 80°; or the tubular member may translate axially relative to the shaft.

In another example, an endoscope may include a first image sensor positioned on a distal-facing wall of a shaft; a second image sensor positioned on a lateral-facing wall of the shaft; and a tubular member having a lumen, the lumen having a distal-end opening and defining a longitudinal axis through a center of the lumen. The tubular member may be movable between a first configuration and a second configuration. In the first configuration of the tubular member, the distal-end opening may be parallel to the distal-facing wall of the shaft. In the second configuration of the tubular member, the longitudinal axis of the lumen may extend through a lateral opening in the shaft.

Any example of an endoscope described herein may further include one or more of the following features: the first image sensor may face a first direction, the second image sensor may face a second direction, and the first and second directions may be about 90° from each other; the endoscope may further include a first light source associated with the first image sensor, and a second light source associated with the second image sensor; the lateral-facing wall of the shaft may be flat, and the distal-facing wall and the lateral-facing wall may be perpendicular to each other; the tubular member may be further movable to a third configuration, and in the third configuration, a medical device positioned within the lumen may be locked relative to the shaft; the tubular member may translate relative to the distal-facing wall and the lateral-facing wall; or in the first configuration of the tubular member, the longitudinal axis of the lumen may be parallel to a longitudinal axis of the shaft.

In yet another example, a method for imaging a patient using an endoscope may include using a first image sensor facing a distal direction to image a first portion of the patient; moving a tubular member having a lumen from a first configuration to a second configuration, the lumen having a distal-end opening and defining a longitudinal axis through a center of the lumen; and using a second image sensor facing a lateral direction to image a second portion of the patient. In the first configuration of the tubular member, the longitudinal axis of the lumen may be parallel to a longitudinal axis of a shaft of the endoscope; and in the second configuration of the tubular member, the longitudinal axis of the lumen may extend through a lateral opening the shaft.

Any method described herein may further include one or more of the following features or steps: the method may further include positioning a medical device within the lumen of the tubular member; the method may further include moving the tubular member from the second configuration to a third configuration, wherein moving the tubular member from the second to the third configuration locks the medical device relative to the shaft; in the first configuration, the distal-end opening of the lumen may be parallel to a distal-end wall of the shaft; or the step of using the second image sensor to image the second portion of the patient may occur while the tubular member is in the second configuration.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to an endoscope having multiple viewing directions. To achieve imaging in multiple directions, the endoscope may have more than one image sensor. In addition, the endoscope may have an elevator (e.g., a tubular member) with an adjustable distal portion, allowing the endoscope to have both a front-exit working channel and a side-exit working channel.

Figure 1:
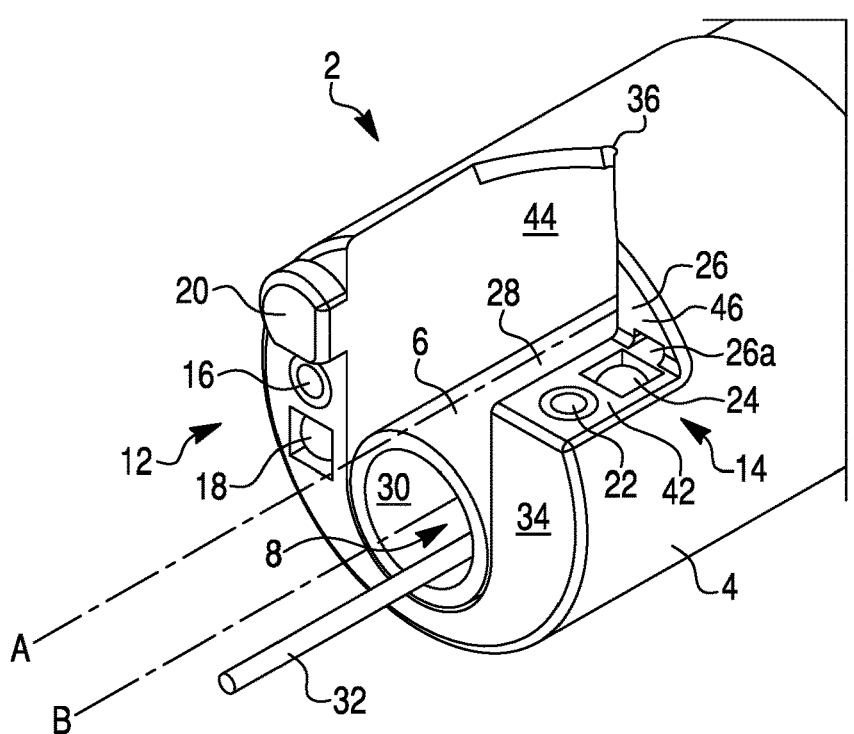
FIG. 1 illustrates a perspective view of the distal end of an endoscope with a tubular member in a straight configuration to create a front-exit working channel, according to one example.

Referring to FIG. 1, an endoscope 2 may include an elongate, flexible, tubular shaft having a distal tip 4. Distal tip 4 may bend left, right, up, and down relative to a proximal portion of the tubular shaft. Endoscope 2 also may include an elevator or tubular member 6 defining a lumen 8, a forward viewing system 12, and a lateral viewing system 14. The tubular shaft (or distal tip 4) of endoscope 2 may define a longitudinal axis A extending in a proximal-distal direction through a center of distal tip 4. In other examples, longitudinal axis A may extend in a proximal-distal direction through distal tip 4 but may be off-center. The forward viewing system 12 may include an image sensor 16, a light source 18, and a lens wash 20. Similarly, the lateral viewing system 14 may include an image sensor 22, a light source 24, and a lens wash 26. Endoscope 2 may be any device used to visually examine the anatomy of a patient and may be used for any suitable procedure. For example, endoscope 2 may be used to examine a patient's gastro-intestinal system, vascular system, respiratory system, or urinary system.

Tubular member 6 may include an elongated tube that extends from a proximal end of the endoscope 2 to a distal end of endoscope 2. Tubular member 6 may include any appropriate biocompatible material, such as polymers, urethane, fluorine-polymer blend, or metals (e.g., stainless steel). Tubular member 6 may include a distal portion 28, shown in the figures, that is bendable relative to a proximal portion (not shown) of tubular member 6. To facilitate bending in a desired region between the proximal portion of tubular member 6 and distal portion 28, tubular member 6 may include a coiled tube portion; a laser-cut pattern that creates a weakened, easily bendable region; a hinge; or any other suitable feature that allows the two portions to bend relative to each other.

Tubular member 6 may have or define a lumen 8. In one example, lumen 8 may have a circular cross-section. In other examples, the cross-section of lumen 8 may be elliptical, polygonal, irregular, or any other suitable shape. Lumen 8 may include a distal-end opening 30 at the distal end of distal portion 28. Lumen 8 (or distal portion 28 of tubular member 6) may define a longitudinal axis B extending through a center of distal portion 28 from a proximal end (e.g., adjacent to the bendable region of tubular member 6) to distal-end opening 30. In other examples, longitudinal axis B may extend in a proximal-distal direction through distal portion 28 but may be off-center. Opening 30 may provide an outlet for a medical device 32, such as a guide wire or other therapeutic or diagnostic device. To position the medical device 32 in lumen 8, as shown in FIG. 1, a distal end of medical device 32 may be inserted into the proximal end of tubular member 6, through lumen 8, and out of distal-end opening 30.

Figure 2:
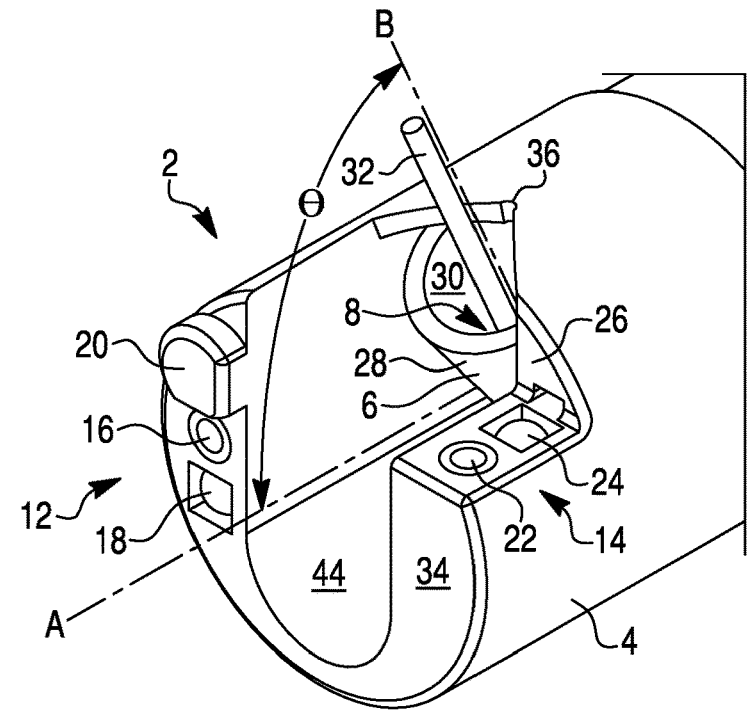
FIG. 2 illustrates a perspective view of the distal end of the endoscope of FIG. 1, with the tubular member in a bent configuration to create a side-exit working channel, according to one example.
Figure 3:
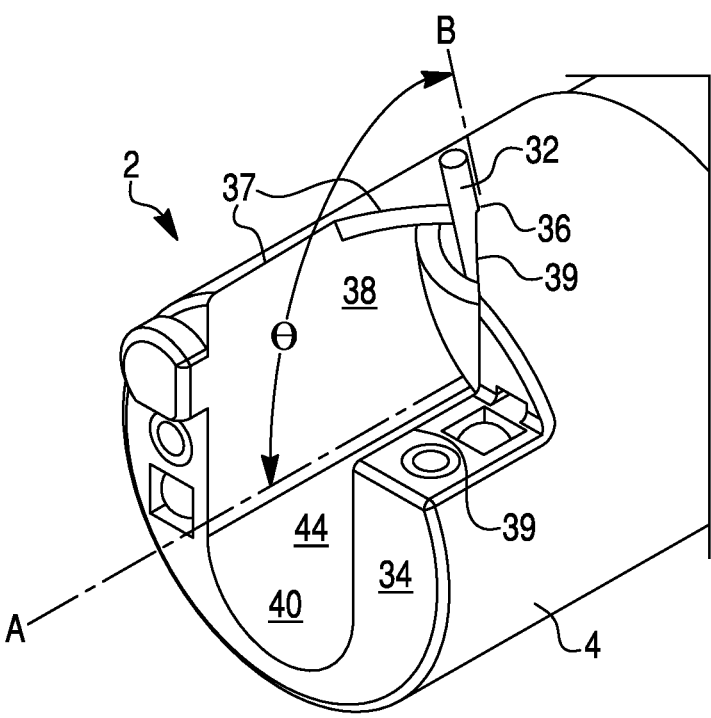
FIG. 3 illustrates a perspective view of the distal end of the endoscope of FIG. 1, with a medical device in the tubular member in a locked position, according to one example.

Distal portion 28 of tubular member 6 may be movable between a first configuration, shown in FIG. 1, and a second configuration, shown in FIG. 2. FIG. 3 illustrates the tubular member in a third configuration. It should be understood that distal portion 28 is further movable between the first and third configurations and the second and third configurations. In the first configuration of FIG. 1, distal-end opening 30 may be parallel to a distal-end wall 34 of distal tip 4. Furthermore, longitudinal axis B of lumen 8 may be parallel to longitudinal axis A of the tubular shaft (or distal tip 4) of endoscope 2. Accordingly, in the first configuration, tubular member 6 may define a working channel (lumen 8) of endoscope 2 having a front exit. The front exit may be proximate to or in a same plane as distal-end wall 34. When tubular member 6 is in the first configuration, forward viewing system 12 may be used to visualize tools, such as medical device 32, extending from tubular member 6.

When tubular member 6 is in the second configuration, shown in FIG. 2, distal-end opening 30 may form an angle with distal-end wall 34 of distal tip 4. Similarly, longitudinal axis B of distal portion 28 of tubular member 6 may form an angle θ with longitudinal axis A of the tubular shaft (or distal tip 4) of endoscope 2. Accordingly, in the second configuration, tubular member 6 may define a working channel (lumen 8) of endoscope 2 having a side or lateral exit. When tubular member 6 is in the second configuration, lateral viewing system 14 may be used to visualize tools, such as medical device 32, extending from tubular member 6.

FIG. 3 illustrates tubular member 6 in a third configuration, which may be referred to as a locked configuration. In the third configuration, movement of medical device 32 relative to tubular member 6 may be inhibited or prevented. In one example, the third configuration may be a position of tubular member 6 when distal portion 28 of tubular member 6 is in its maximally bent position (with a medical device 32 extending from distal-end opening 30) relative to the longitudinal axis of distal tip 4 of endoscope 2. In other words, in the third configuration, angle θ may be greater than angle θ when tubular member 6 is in the first or second configurations. Distal tip 4 may include a notch or indentation 36 sized to receive and secure medical device 32 relative to distal tip 4 of the tubular shaft. Indentation 36 may be distal-facing. When tubular member 6 moves to the third configuration, medical device 32 may be pressed between a wall of distal portion 28 and indentation 36 and may form a press-fit attachment with distal tip 4 via indentation 36. In the third configuration of tubular member 6, as will be described further below, medical device 32 may be held securely while a catheter or other medical device is advanced over medical device 32 within lumen 8. Advancement of a medical device over device 32 may occur, however, in any of the first, second, or third configurations.

Figure 4:
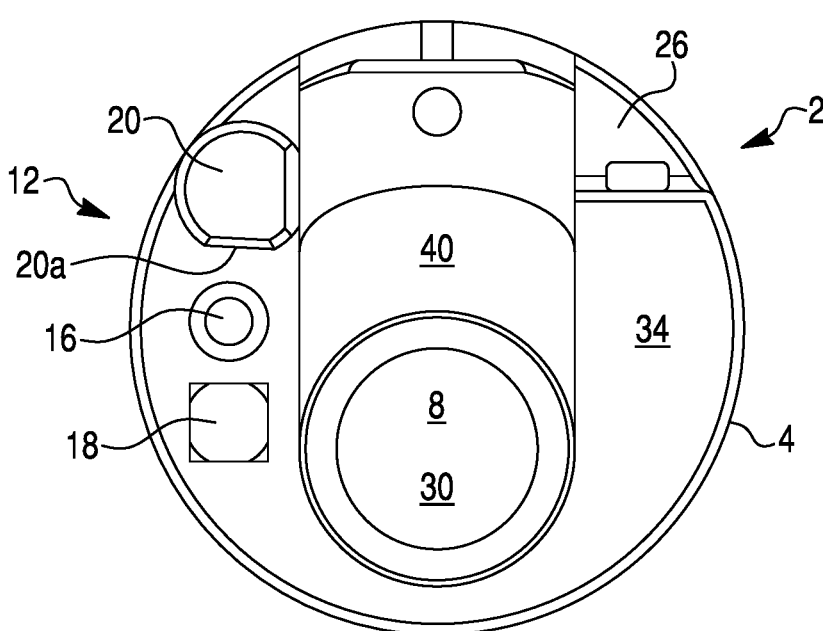
FIG. 4 illustrates a distal-end view of the endoscope of FIG. 1, according to one example.
Figure 5:
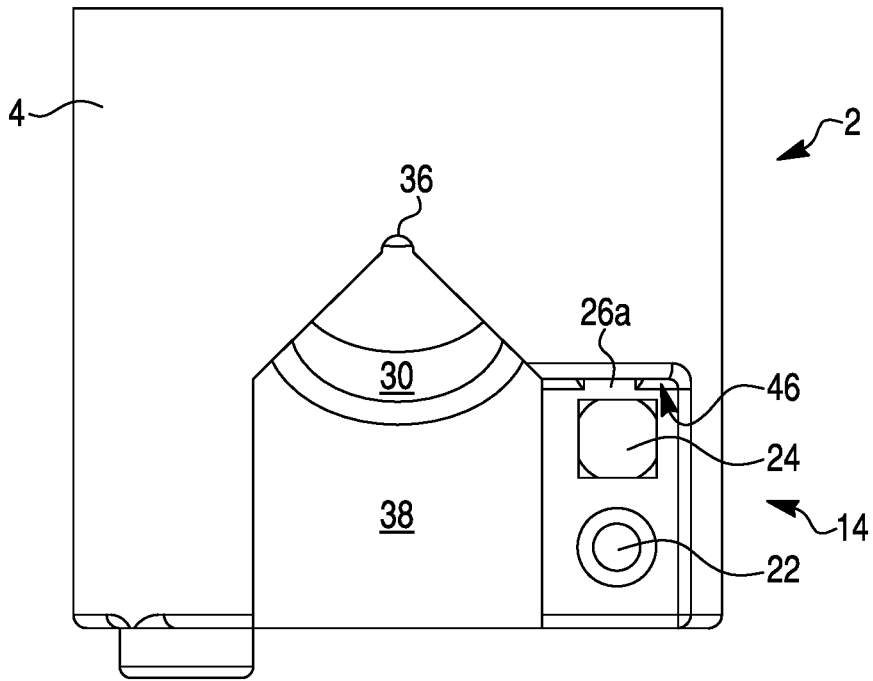
FIG. 5 illustrates a top view of the tip of the endoscope of FIG. 2, according to one example.

Referring to FIGS. 3, 4, and 5, the walls of distal tip 4 of the tubular shaft of endoscope 2 may include a lateral opening 38 and a distal opening 40 (in distal-end wall 34) to allow tools exiting distal-end opening 30 of tubular member 6 to access an exterior of endoscope 2. Openings 38 and 40 combine to form a single opening at distal tip 4 that is both distal facing and side facing. Lateral opening 38 may extend proximally from distal-end wall 34. From distal-end wall 34, a first side 37 and a second side 39 of lateral opening 38 may extend parallel to each other for a portion of the length (in a proximal-distal direction) of lateral opening 38. The two sides 37, 39 may then move proximally and towards each other towards indentation 36. Indentation 36 may be a part of lateral opening 38 and may be defined on a proximal side by a curved portion of the wall of distal tip 4 extending between first and second sides 37, 39.

Distal opening 40 may be the distal end of a lumen 44 that extends in a longitudinal direction through distal tip 4 of the tubular shaft of endoscope 2. Referring to the view of FIG. 4, distal opening 40 may extend from a top edge of distal tip 4, where it connects and is continuous with lateral opening 38. From lateral opening 38, distal opening 40 may extend towards the opposite wall of distal tip 4 (towards the bottom of the page when viewing FIG. 4). At its bottom edge (in the view of FIG. 4), distal opening 40 may be curved so that the walls of distal-end wall 34 around distal opening 40 form a U-shape. The U-shape of distal opening 40 may allow distal portion 28 of tubular member 6 to extend to the fully straight, first configuration shown in FIGS. 1 and 4. In one example, the curvature of distal opening 40 at the bottom may match the curvature of the outer surface of tubular member 6.

When tubular member 6 is moved from the first configuration to the second or third configurations, medical device 32 may continually have access to an exterior of endoscope 2 via distal opening 40 and lateral opening 38. For example, in the first configuration shown in FIG. 1, medical device 32 may access an exterior of endoscope 2 through distal opening 40. As tubular member 6 approaches the second configuration shown in FIG. 2, medical device 32 may pass through lateral opening 38 to extend from lumen 8 to the exterior of endoscope 2. Accordingly, distal opening 40 and lateral opening 38 provide a pathway so that tools extending from the distal-end opening 30 of lumen 8 can access the exterior of endoscope 2. Described another way, when tubular member 6 is in the first configuration, longitudinal axis B of tubular member 6 may extend through distal opening 40. However, in the second configuration of tubular member 6, longitudinal axis B may extend through lateral opening 38. In the third configuration of tubular member 6, longitudinal axis B may extend through a wall of distal tip 4 if longitudinal axis B passes through a center of lumen 8 (e.g., as shown in FIG. 3). However, if longitudinal axis B is off-center, it also may extend through lateral opening 38 when tubular member 6 is in the third configuration.

Tubular member 6 may be moved through its range of motion (e.g., between first, second, and third configurations) by any mechanism known in the art. In one example, a wire (not shown) may be secured to the exterior of distal portion 28 (e.g., by a ring around tubular member 6, by adhesive, by solder, etc.) and may travel proximally towards the proximal end of tubular member 6. A user may pull the wire proximally to move distal portion 28 from the first configuration towards the second or third configurations. In other words, proximal movement of the wire may cause distal portion 28 to bend further relative to distal tip 4 of endoscope 2 (e.g., may cause angle θ to increase). For convenience, the bending motion of distal portion 28 that increases angle θ will be referred to herein as "proximal" movement of distal portion 28. Conversely, the user may push a wire or other mechanism distally to move distal portion 28 from the second or third configurations towards the first configuration. In other words, distal movement of the wire may cause distal portion 28 to bend less relative to distal tip 4 of endoscope 2 (e.g., may cause angle θ to decrease) and move towards a position in which longitudinal axis B is parallel to longitudinal axis A. For convenience, this straightening motion of distal portion 28 that deceases angle θ will be referred to herein as "distal" movement of distal portion 28.

In one example, distal portion 28 of tubular member 6 may have a range of motion of about 85°. As used herein, "about" means plus or minus 5%, inclusive. Depending on the example, the range of motion may be defined as the angle θ between the first and second configurations (e.g., between FIGS. 1 and 2) or the angle θ between the first and third configurations (e.g., between FIGS. 1 and 3). When the range of motion is the angle θ between the first and second configurations, the range of motion may include any position of distal portion 28 that allows medical device 32 to freely move while protruding from distal-end opening 30 of distal portion 28. When the range of motion is the angle θ between the first and third configurations, the range of motion may include any position of distal portion 28 that allows medical device 32 to protrude from distal-end opening of distal portion 28, whether the medical device 32 is freely movable or locked.

In other examples, distal portion 28 may have a range of motion of about 70°, about 75°, about 80°, or about 90°. In yet other examples, the range of motion of distal portion 28 may be at least 80°, at least 85°, at least 90°, at least 95°, less than 95°, less than 90°, less than 85°, or less than 80°. To increase the range of motion from that shown in the figures, lateral opening 38 of distal tip 4 may be extended proximally to allow distal portion 28 and any medical device 32 within its lumen to bend further in a proximal direction. Alternatively, tubular member 6 may translate or slide distally within lumen 44 of the tubular shaft, sufficiently to permit distal portion 28 to have the desired range of motion. To decrease the range of motion, lateral opening 38 of distal tip 4 may be shortened (e.g., indentation 36 may be moved distally) to prevent distal portion 28 and any medical device 32 within its lumen to bend as far in a proximal direction. Alternatively, tubular member 6 may translate or slide proximally within lumen 44 of the tubular shaft, sufficiently to reduce the range of motion of distal portion 28.

FIG. 4 illustrates a distal-end view of endoscope 2 showing the forward viewing system 12, and FIG. 5 illustrates a top view of distal tip 4 showing lateral viewing system 14. Image sensors 16, 22 may be any sensor that detects light and conveys information to allow for remote viewing of an image, such as CMOS or CCD sensors. Light sources 18, 24 may emit any type of light to illuminate the area proximate to their associated image sensors 16, 22. The lens washes 20, 26 may provide an outlet for water, saline, or other fluid used to clean the respective image sensors 16, 22 and/or light sources 18, 24. Lens wash 20 may include an exit nozzle 20a for fluid to exit lens wash 20. Similarly, lens wash 26 may include an exit nozzle 26a for fluid to exit lens wash 26.

Referring to the distal-end view of FIG. 4, the components of forward viewing system 12 may be positioned on distal-end wall 34 of distal tip 4/tubular shaft/endoscope 2. Distal-end wall 34 may be perpendicular to longitudinal axis A. Image sensor 16 may be positioned towards the left side of distal opening 40. Light source 18 may be positioned below image sensor 16 (in the view of FIG. 4) and may be associated with image sensor 16 by being positioned to illuminate an area proximate to image sensor 16. Lens wash 20 may be positioned above image sensor 16 (in the view of FIG. 4) and may be configured to release fluid to clean image sensor 16 and/or light source 18. However, image sensor 16, light source 18, and lens wash 20 may be positioned in any other order or configuration relative to each other. For example, two or more of the components may be positioned next to each other (side-by-side in the view of FIG. 4). Alternatively, one or more of image sensor 16, light source 18, and lens wash 20 may be positioned on the opposite side of distal opening 40 (e.g., on the portion of distal-end wall 34 to the right of distal opening 40 in the view of FIG. 4, closer to viewing system 14). In an alternative example, one or more of image sensor 16, light source 18, and lens wash 20 may be positioned on a distal-facing wall of the tubular shaft of endoscope 2 that is not at the distal-most end of endoscope 2 (e.g., on a distal wall 46 (see FIG. 1) or another distal-facing wall).

Referring to the top view of FIG. 5, image sensor 22 may be positioned proximate to (and proximal to) distal-end wall 34, and light source 24 may be positioned proximal to image sensor 22. Image sensor 22 and light source 24 may be positioned on a lateral wall 42 of distal tip 4/tubular shaft/endoscope 2. Light source 24 may be associated with image sensor 22 by being positioned to illuminate an area proximate to image sensor 22. Lateral wall 42 may be any lateral-facing wall and may be curved or flat. Referring to FIGS. 1-3, in one example, lateral wall 42 may be a flat wall extending proximally from distal-end wall 34. In another example, lateral wall 42 may be a curved outer surface of distal tip 4. Referring back to FIG. 5, lens wash 26 may be positioned proximal to light source 24 on distal wall 46 and may include an outlet through which saline or another fluid may be released along lateral wall 42 to clean image sensor 22 and/or light source 24. Image sensor 22, light source 24, and lens wash 26 may be positioned in any other order or configuration relative to each other. Alternatively, one or more of these components may be positioned on the opposite side of lateral opening 38 (e.g., on the left of lateral opening 38 in the view of FIG. 5).

Image sensor 16 on distal-end wall 34 may face a distal direction. Accordingly, when tubular member 28 is in the first configuration and when it is moving proximally towards the second configuration, image sensor 16 may be used to view medical device 32 and any other tools extending from distal-end opening 30. In contrast, image sensor 22 in lateral wall 42 may face a lateral direction. Accordingly, when tubular member 28 is approaching the second configuration or when it is in the second or third configuration, image sensor 22 may be used to view medical device 32 and any other tools extending from distal-end opening 30.

In one example, distal-end wall 34 (or any other distal-facing wall that includes image sensor 16) and lateral wall 42 (or any other lateral-facing wall that includes image sensor 22) may be perpendicular to each other. The angles described herein between the two walls may correspond to the angles between the viewing directions of image sensors 16, 22. In another example, distal-end wall 34 and lateral wall 42 (and the corresponding viewing directions of image sensors 16, 22) may deviate from 90° and may be positioned about 90° relative to each other. In other examples, the two walls may be positioned about 85°, about 80°, or about 75° relative to each other. In yet another example, the two walls may be positioned at least 90° or less than 90° relative to each other.

In one example, the viewing directions of image sensors 16, 22 can be adjusted relative to their respective walls. For example, the viewing direction of image sensor 16 may be adjusted to pivot along one or more axes relative to its default position within distal-end wall 34, with the default position being a position facing the same direction as distal-end wall 34. Similarly, the viewing direction of image sensor 22 may be adjusted to pivot along one or more axes relative to its default position within lateral wall 42, with the default position being a position facing the same direction as lateral wall 42.

In an exemplary procedure using endoscope 2, distal tip 4 may be inserted through a patient's mouth, esophagus, stomach, and duodenum during a first portion of the procedure. Forward viewing system 12 may be used during the first portion of the procedure to help the user navigate through the patient's anatomy. While navigating to the duodenum, tubular member 6 may be in a first configuration to allow medical device 32 (e.g., a guide wire) or other tools to move distally past the distal-end wall 34 of distal tip 4. For example, a guide wire may be inserted from the stomach and through the pylorus to help navigate the distal tip 4 from the stomach into the duodenum.

Near the duodenal papilla, the user may use lateral viewing system 14 to help locate the duodenal papilla. Using guidance from lateral viewing system 14, medical device 32 (e.g., a guide wire) may be inserted through the duodenal papilla and into the patient's pancreatic duct. To aid in inserting medical device 32 into the duodenal papilla, tubular member 6 may be moved to the second configuration to allow medical device 32 to exit the lateral side of endoscope 2. Endoscope 2 and its distal tip 4 may remain in a substantially straight configuration within the duodenum while medical device 32 extends out of distal-end opening 30 from the lateral side of distal tip 4. Once medical device 32 is inserted into the pancreatic duct, tubular member 6 may be moved to the third configuration to lock medical device 32 relative to distal tip 4 of the tubular shaft. In one example, both viewing systems 12, 14 may be used simultaneously during any portion of a procedure.

A cannula (not shown) then may be inserted through lumen 8 of tubular member 6 over medical device 32. Once the cannula reaches distal tip 4, tubular member 6 may be moved proximally to the second configuration (or past the second configuration towards the first configuration) to unlock medical device 32. The cannula may then be passed out of distal-end opening 30 and into the pancreatic duct over medical device 32 to cannulate the pancreatic duct. A contrast agent may be injected into the pancreatic duct, and fluoroscopy images may be taken to study the bile ducts, the gallbladder, and the pancreatic duct. If desired, other tools may be inserted through the tubular member 6 and/or cannula into the pancreatic duct to treat pancreatic or biliary conditions.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A medical device, comprising:
a shaft having a longitudinal axis;
an image sensor; and
an elevator having a lumen, the lumen having a distal-end opening and defining a longitudinal axis through a center of the lumen, the elevator being movable between a first configuration and a second configuration;
wherein in the first configuration of the elevator, the distal-end opening is positioned to permit an instrument to extend through a front opening of the shaft; and
wherein in the second configuration of the elevator, the distal-end opening is positioned to permit an instrument to extend through a lateral opening of the shaft, wherein a portion of the shaft is positioned over and blocking at least a portion of the distal-end opening of the elevator when the elevator is in the second configuration.

2. The medical device of claim 1, wherein in the first configuration of the elevator, the longitudinal axis of the lumen is substantially parallel to the longitudinal axis of the shaft.

3. The medical device of claim 1, wherein the image sensor is disposed on a wall of the shaft.

4. The medical device of claim 1, wherein the image sensor comprises a first image sensor facing a first direction, and a second image sensor facing a second direction.

5. The medical device of claim 4, wherein the first image sensor is disposed on a distal-facing wall of the shaft, and the second image sensor is disposed on a lateral-facing wall of the shaft.

6. The medical device of claim 5, wherein in the first configuration of the elevator, the distal-end opening is substantially parallel to the distal-facing wall of the shaft, and the elevator is configured to translate distally of the distal-facing wall of the shaft.

7. The medical device of claim 1, further comprising the instrument disposed within the elevator, and wherein in the first configuration of the elevator, the instrument is configured to translate distally through the front opening of the shaft.

8. The medical device of claim 7, wherein the shaft comprises an indentation sized and shaped to receive a portion of the instrument therein.

9. The medical device of claim 8, wherein the indentation is configured to form a press-fit attachment with the portion of the instrument, thereby locking the elevator in the second configuration relative to the shaft.

10. The medical device of claim 8, wherein the shaft comprises a first wall and a second wall that at least partially define the lateral opening, and wherein the indentation is disposed between the first wall and the second wall.

11. The medical device of claim 10, wherein the first wall and the second wall of the shaft are configured to guide the instrument toward the indentation in response to the elevator moving from the first configuration to the second configuration.

12. The medical device of claim 1, further comprising an actuator mechanism configured to move the elevator relative to the shaft between the first configuration and the second configuration.

13. A medical device, comprising:
a shaft having a longitudinal axis;
an image sensor;
an elevator disposed in the shaft, wherein the elevator comprises a lumen having a distal-end opening and defining a longitudinal axis through a center of the lumen; and
an actuator mechanism configured to move the elevator between a first configuration and a second configuration relative to the shaft;
wherein in the second configuration, a portion of the shaft is positioned over and blocking at least a portion of the distal-end opening of the elevator.

14. The medical device of claim 13, further comprising:
an instrument disposed within the lumen of the elevator;
wherein in the first configuration, the distal-end opening is positioned to permit the instrument to extend through a front opening of the shaft; and
wherein in the second configuration, the distal-end opening is positioned to permit the instrument to extend through a lateral opening of the shaft.

15. The medical device of claim 14, wherein the shaft comprises an indentation sized and shaped to receive a portion of the instrument therein.

16. The medical device of claim 15, wherein the indentation is configured to form a press-fit attachment with the portion of the instrument, thereby locking the elevator in the second configuration relative to the shaft.

17. The medical device of claim 13, wherein the image sensor comprises a first image sensor facing a first direction, and a second image sensor facing a second direction.

18. The medical device of claim 17, wherein the first image sensor is disposed on a distal-facing wall of the shaft, and the second image sensor is disposed on a lateral-facing wall of the shaft.

19. The medical device of claim 18, wherein in the first configuration, the distal-end opening is substantially parallel to the distal-facing wall of the shaft, and the elevator is configured to translate distally of the distal-facing wall of the shaft.

20. A medical device comprising:

a shaft having a longitudinal axis;

an image sensor;

an elevator disposed in the shaft, wherein the elevator comprises a lumen having a distal-end opening and defining a longitudinal axis through a center of the lumen;

an actuator mechanism configured to move the elevator between a first configuration and a second configuration relative to the shaft; and an instrument disposed within the lumen of the elevator;

wherein in the first configuration, the distal-end opening is positioned to permit the instrument to extend through a front opening of the shaft and not a lateral opening of the shaft; and wherein in the second configuration, the distal-end opening is positioned to permit the instrument to extend through the lateral opening of the shaft and not the front opening of the shaft, and a portion of the shaft is positioned over and blocking at least a portion of the distal-end opening of the elevator;

wherein the shaft comprises an indentation sized and shaped to receive a portion of the instrument therein;

wherein the indentation is configured to form a press-fit attachment with the portion of instrument, thereby locking the elevator in the second configuration relative to the shaft.

* * * * *